United States Patent
Bornzin et al.

(10) Patent No.: US 9,895,531 B2
(45) Date of Patent: Feb. 20, 2018

(54) PROTECTIVE PATCH FOR PROTECTING THE IMPLANT SITE OF A TRIAL NEUROSTIMULATION LEAD

(71) Applicant: PACESETTER, INC., Sylmar, CA (US)

(72) Inventors: Gene A. Bornzin, Simi Valley, CA (US); Jenner Joseph, Santa Clarita, CA (US); Katie Hoberman, Winnetka, CA (US); Zoltan Somogyi, Simi Valley, CA (US); Chris Condit, Plano, TX (US); Heidi Hellman, Los Angeles, CA (US)

(73) Assignee: PACESETTER, INC., Sylmar, CA (US)

( * ) Notice: Subject to any disclaimer, the term of this patent is extended or adjusted under 35 U.S.C. 154(b) by 897 days.

(21) Appl. No.: 14/251,436

(22) Filed: Apr. 11, 2014

(65) Prior Publication Data

US 2015/0290455 A1    Oct. 15, 2015

(51) Int. Cl.
*A61F 13/00* (2006.01)
*A61N 1/05* (2006.01)
*A61F 13/02* (2006.01)

(52) U.S. Cl.
CPC ...... *A61N 1/0551* (2013.01); *A61F 13/00051* (2013.01); *A61F 13/023* (2013.01)

(58) Field of Classification Search
CPC ........ A61N 1/375; A61N 1/36; A61N 1/0492; A61N 1/05; A61N 1/0592; A61N 1/0551; A61N 2/00; A61N 2/02; A61N 5/00; A61N 5/06; A61F 13/0051; A61F 13/0068; A61F 15/004; A61F 15/008
See application file for complete search history.

(56) References Cited

U.S. PATENT DOCUMENTS

| | | | |
|---|---|---|---|
| 4,271,840 A * | 6/1981 | Lattin | A61N 1/3752 128/899 |
| 7,136,703 B1 | 11/2006 | Cappa et al. | |
| 7,177,684 B1 | 2/2007 | Kroll et al. | |
| 7,207,947 B2 | 4/2007 | Koh et al. | |
| 8,162,841 B2 | 4/2012 | Keel et al. | |
| 8,512,240 B1 | 8/2013 | Zuckerman-Stark et al. | |
| 8,600,500 B1 | 11/2013 | Rosenberg et al. | |
| 2005/0209664 A1* | 9/2005 | Hunter | A61L 31/10 607/115 |

(Continued)

OTHER PUBLICATIONS

Storm, Hanne, "Changes in skin conductance as a tool to monitor nociceptive stimulation and pain," Curr Opin Anaesthesiol. 2008;21:796-804.

*Primary Examiner* — Jacqueline Stephens

(57) ABSTRACT

A protective patch or bandage is provided for use with an implantable trial neurostimulation lead for implant within a patient. In one example, the lead is routed through the patch to a trial neurostimulation generator. In another example, the patch includes an internal electrical connector for connecting the trial neurostimulation lead to a connection line from the trial neurostimulation generator. In either case, the patch is sealed over an implant site to protect and hygienically isolate the site. A central chamber of the patch is provided to hold medical gauze and to further hold a coiled portion of the neurostimulation lead. In some examples, the patient can shower while wearing the protective patch.

7 Claims, 14 Drawing Sheets

(56) References Cited

U.S. PATENT DOCUMENTS

| | | |
|---|---|---|
| 2009/0187087 A1 | 7/2009 | Turcott |
| 2009/0299435 A1 | 12/2009 | Gliner et al. |
| 2010/0331921 A1 | 12/2010 | Bornzin et al. |
| 2013/0325083 A1 | 12/2013 | Bharmi et al. |
| 2014/0128948 A1 | 5/2014 | Clark et al. |

* cited by examiner

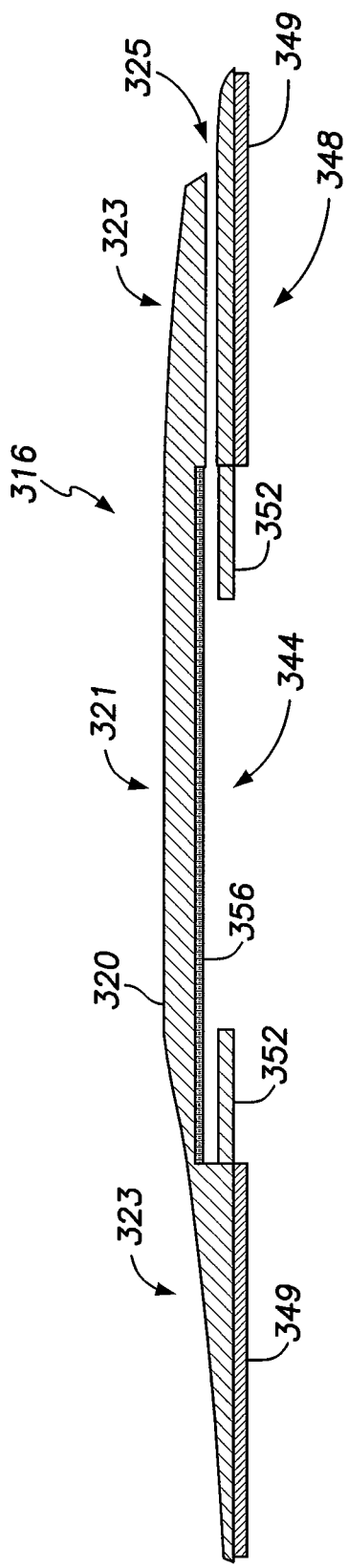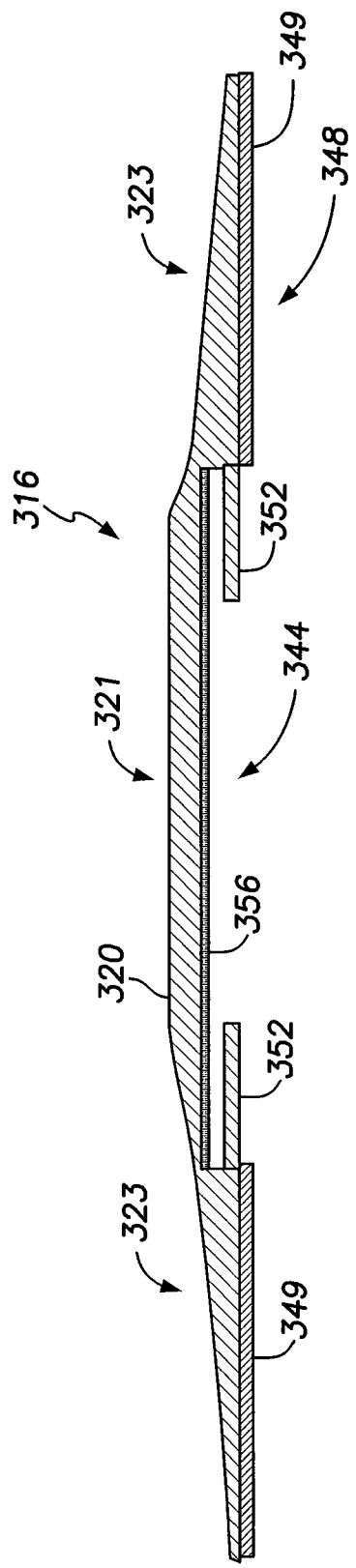

OVERVIEW OF TECHNIQUES FOR USE WITH PROTECTIVE PATCH WITHOUT AN INTERNAL CONNECTOR

PROVIDE A PROTECTIVE PATCH WITH:

A TOP PORTION HAVING AN OPENING FOR PASSAGE OF AN IMPLANTABLE TRIAL SCS LEAD FROM A HEADER OF A TRIAL SCS GENERATOR/CONTROLLER INTO AN INNER CHAMBER OF THE PATCH;

A BOTTOM PORTION CONFIGURED TO BE DETACHABLY AFFIXED OR ADHERED TO PATIENT SKIN OVER AN IMPLANT ENTRY SITE AND HAVING A BOTTOM OPENING FOR PASSAGE OF THE LEAD FROM THE INNER CHAMBER INTO TISSUES OF THE PATIENT AT THE IMPLANT SITE; AND

AN ADHESIVE FORMED ON A PERIPHERAL PORTION OF A BOTTOM SURFACE OF THE PATCH FOR SEALING THE PATCH OVER THE IMPLANT SITE — 900

IMPLANT A DISTAL END OF THE SCS LEAD INTO THE PATIENT AT THE IMPLANT SITE AND FEED THE PROXIMAL END OF THE LEAD THROUGH THE PROTECTIVE PATCH FOR CONNECTION TO THE HEADER OF THE SCS DEVICE AROUND ANTIMICROBIAL GAUZE — 902

AFFIX OR ADHERE THE PATCH TO THE SKIN AROUND THE IMPLANT SITE USING THE ADHESIVE TO PROTECT AND SEAL THE SITE — 904

DELIVER TRIAL NEUROSTIMULATION DURING A TRIAL INTERVAL, THEN REMOVE AND DISCARD THE PATCH, LEAD AND HEADER AND, IF ADEQUATE PAIN MITIGATION WAS ACHIEVED DURING THE TRIAL PERIOD, IMPLANT A PERMANENT (I.E. CHRONIC OR LONG-TERM) NEUROSTIMULATION DEVICE/LEAD SYSTEM — 906

FIG. 14

OVERVIEW OF TECHNIQUES FOR USE WITH PROTECTIVE PATCH WITH AN INTERNAL CONNECTOR

PROVIDE A PROTECTIVE PATCH WITH:

A TOP PORTION EQUIPPED TO RECEIVE AN END OF A CONNECTION LINE OF A TRIAL SCS DEVICE;

A BOTTOM PORTION CONFIGURED TO BE DETACHABLY AFFIXED OR ADHERED TO PATIENT SKIN OVER AN IMPLANT ENTRY SITE AND HAVING AN OPENING FOR RECEIVING ONE END OF AN IMPLANTABLE TRIAL SCS LEAD;

AN ELECTRICAL CONNECTOR EQUIPPED TO CONNECT THE END OF THE CONNECTION LINE OF THE TRIAL DEVICE WITH THE END OF THE IMPLANTABLE TRIAL SCS LEAD; AND

AN ADHESIVE FORMED ON A PERIPHERAL PORTION OF A BOTTOM SURFACE OF THE PATCH FOR SEALING THE PATCH OVER THE IMPLANT SITE AROUND ANTIMICROBIAL GAUZE

1000

IMPLANT A DISTAL END OF THE SCS LEAD INTO THE PATIENT AT THE IMPLANT SITE AND CONNECT THE PROXIMAL END OF THE LEAD TO A DISTAL END OF THE CONNECTION LINE FROM THE SCS DEVICE USING THE ELECTRICAL CONNECTOR OF THE PROTECTIVE PATCH

1002

AFFIX OR ADHERE THE PATCH TO THE SKIN AROUND THE IMPLANT SITE USING THE ADHESIVE TO PROTECT AND SEAL THE SITE

1004

DELIVER TRIAL NEUROSTIMULATION DURING A TRIAL INTERVAL, THEN REMOVE AND DISCARD THE PATCH AND LEAD AND, IF ADEQUATE PAIN MITIGATION WAS ACHIEVED DURING THE TRIAL PERIOD, IMPLANT A PERMANENT (I.E. CHRONIC OR LONG-TERM) NEUROSTIMULATION DEVICE/LEAD SYSTEM

PROTECTIVE PATCH FOR PROTECTING THE IMPLANT SITE OF A TRIAL NEUROSTIMULATION LEAD

FIELD OF THE INVENTION

The disclosure generally relates to trial implantable neurostimulation leads and devices and to accessories for use therewith.

BACKGROUND OF THE INVENTION

Implantable neurostimulation devices can be employed to manage pain arising from a variety of neuropathies and provide a valuable treatment for chronic intractable neuropathic pain. Neurostimulation is also being investigated for cardiac applications such as treatment of heart failure and atrial fibrillation. To these various ends, a spinal cord stimulation (SCS) device or other neurostimulator may be implanted within the body to deliver electrical pulses to nerves or other tissues. The neurostimulator typically includes a small pulse generator device similar to a pacemaker but equipped to send electrical pulses to leads mounted along the nerves near the spinal cord or elsewhere within the body. For SCS, the generator is often implanted in the abdomen. The stimulation leads may include thin wires or paddles for delivering electrical pulses to patient nerve tissues. An external controller, similar to a remote control device, may be provided to allow the patient to control or adjust the neurostimulation. Currently, prior to permanent (i.e. chronic or long-term) implant of a neurostimulator, the patient undergoes a trial period during which he or she is implanted with a percutaneous lead that is externalized and connected to a trial neurostimulation control device or instrument, which the patient carries with him or her.

In United States, patients typically have the trial neurostimulation system for less than a week. In Europe, the trial period can last up to a month. Unfortunately, current trial neurostimulation devices are problematic. The implanted percutaneous lead can be inadvertently pulled from the epidural space or may migrate from the implant site such that the patient will receive no therapeutic benefit. This can result in a failed trial. Current systems are often quite cumbersome. Typically, the lead is taped to the skin at the exit point. A long extension connects the lead with the trial neurostimulator, which is worn on a belt. The extension and lead are packaged within a bulky bandage and tape arrangement that is uncomfortable and irritating for the patient. With such devices, the patient is not allowed to shower. The trial experience can often be very unpleasant, particularly for patients who do not tolerate being "taped up." It is believed that the "annoyance factor" can lead to a failed trial because the patients become "fed up" with the process. As a result, many patients who might benefit from SCS or other forms of neurostimulation do not receive such devices.

Accordingly, it would be desirable to provide improved trial neurostimulation devices and accessories for use therewith that address these or other problems, and it is to this end that at least some aspects of the disclosure are directed.

SUMMARY OF THE INVENTION

In an exemplary embodiment, a protective "guardian" patch is provided for use with an implantable trial neurostimulation lead for implant within a patient. The patch comprises a top portion having an opening for passage of the implantable trial neurostimulation lead into an inner chamber of the patch, and a bottom portion configured to be detachably affixed or adhered to patient skin over a trial lead implant entry site. The bottom portion includes an opening for passage of the implantable lead from the inner chamber of the patch into the tissues of the patient at the implant site, i.e. at the exit point of the lead from the skin of the patient. The bottom portion of the patch may also include a peripheral surface with a medical skin adhesive for sealing the patch over the implant site. In use, the trial neurostimulation lead is fed through the protective patch so that, after implant of the lead, the patch may be sealed over the implant site to hygienically isolate and protect the site, while the free end of the lead is then connected to a trial neurostimulation generator/controller device or a header for use therewith. Herein, for brevity, the trial neurostimulation generator/controller device will often be referred to as a trial neurostimulation device or a trial SCS device.

In an illustrative example, the top portion of the patch tightly seals around the lead so the patient may shower without water reaching the implant site. That is, it provides a water resistant medical seal. The seal also prevents the ingress of bacteria into the lead entry site. The chamber includes a material such as medical gauze for absorbing blood or other fluids emanating from the implant site. The gauze may be treated with antibacterial or antimicrobial agents. The chamber also preferably accommodates a coiled length of the implantable lead. In this regard, the neurostimulation device may be conveniently taped to the patient near the patch with any excess portions of the lead coiled and stowed within the patch. The coiled portion also provides for a self-contained strain relief loop so that, if the lead is inadvertently tugged, the lead will uncoil within the patch by an amount sufficient to relieve the strain while the end of the lead implanted within the body remains unaffected. This helps prevent the lead from being pulled from or migrating from the implant site. The chamber can be provided with suitable retention wings or tabs or other features to hold the coiled portion of the lead. The protective patch may be formed of flexible molded polymer. The trial neurostimulation device itself may be provided with a disposable header device for lead connection so that, following the neurostimulation trial, the header and lead, as well as the protective patch, can be discarded, while the trial neurostimulation device controller is reused. This helps prevent any contamination issues that might otherwise arise if the implantable lead were directly connected to the trial neurostimulation device.

In another exemplary embodiment, a protective patch is provided for use with an implantable trial neurostimulation device equipped with a connection line. In this embodiment, the patch comprises a top portion equipped to receive an end of the connection line of the trial neurostimulation device and a bottom portion configured to be detachably adhered to patient skin over a trial lead implant site. The bottom portion has an opening for receiving one end of the implantable trial neurostimulation lead. The patch also has an electrical connector equipped to connect the end of the connection line of the trial neurostimulation device with the end of the implantable trial neurostimulation lead. That is, the patch includes means for electrically connecting the line from the neurostimulation device to the trial lead that is implanted within the patient so that stimulation pulses may be routed through the patch and into the tissues of the patient. A peripheral surface of the bottom portion of the patch is provided with an adhesive for sealing the patch over the implant site during the trail.

In use, the trial neurostimulation lead is fed into the bottom portion of the patch for connection to one end of the electrical connector. The connection line from the neurostimulation device is fed into the top portion for connection to an opposing end of the electrical connector. Alternatively, the top portion of the patch includes a connection terminal so that the connection line from the neurostimulation device need not be fed into the patch itself. Rather, the connection line is simply connected into the connection terminal, which feeds stimulation pulses from the neurostimulation device to the internal connector that is coupled to the implantable lead for feeding those pulses into the tissues of the patient. In either case, after implant of the lead, the patch is sealed over the implant site to protect the site. An internal chamber may be provided that includes medical gauze. The chamber also preferably accommodates a coiled length of the implantable lead to stow excess portions of the lead within the patch. Although the trial neurostimulation device may again be provided with a disposable header such is not required. With this configuration, the implantable lead is never directly connected to the trial neurostimulation device and so there are no issues regarding contamination of the trial neurostimulation device.

In another exemplary embodiment, a trial neurostimulation device is provided for use with an implantable neurostimulation lead for implant within a patient. The trial device comprises: a trial neurostimulation controller and a header component configured to be detachably coupled to the trial neurostimulation controller. The header component includes a connector configured to electrically couple the trial neurostimulation controller to the implantable neurostimulation lead. This trial neurostimulation device may be used in conjunction with one of the aforementioned protective patches, or separately, if warranted.

System, apparatus and method examples are described below.

BRIEF DESCRIPTION OF THE DRAWINGS

The above and further features, advantages and benefits of the invention will be apparent upon consideration of the descriptions herein taken in conjunction with the accompanying drawings, in which:

FIG. 6 is a side cross-sectional view of another example of the protective patch of FIG. 1, particularly showing an opening within a top portion thereof for passage of the SCS lead;

FIG. 7 is another side cross-sectional view of the exemplary protective patch of FIG. 6, taken along an axis wherein the opening within the top portion thereof is not visible;

FIG. 14 summarizes techniques for use with the trial SCS device and protective patch of FIG. 1; and FIG. 15 summarizes techniques for use with the trial SCS device and protective patch of FIG. 8.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Trial Neurostimulation System with Protective Implant Site Patch

Figure 1:
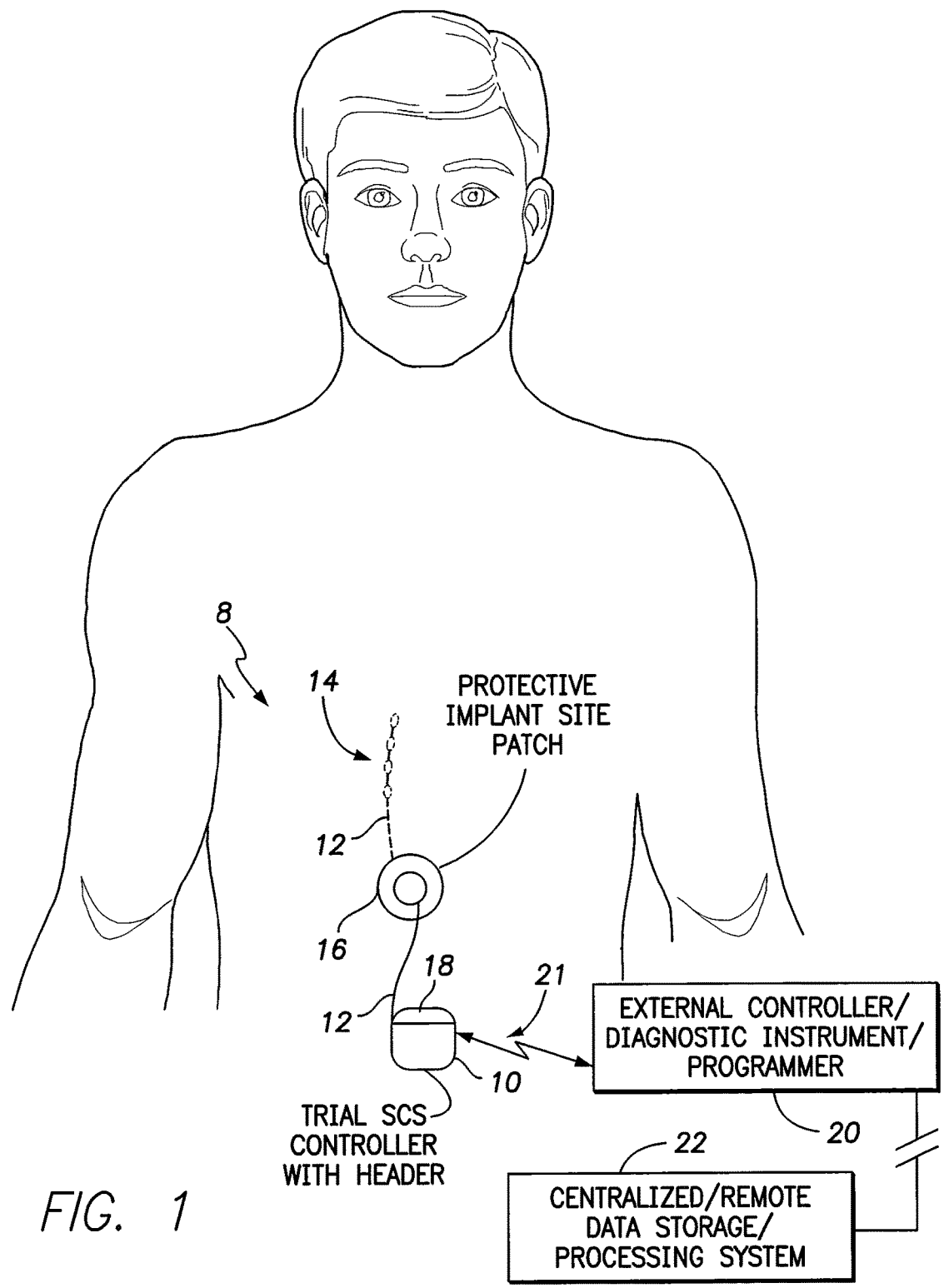
FIG. 1 illustrates an exemplary protective patch for use with a trial SCS device wherein an implantable trial neurostimulation lead is routed from the SCS device through the protective patch and into the tissues of the patient at an implant site covered by the patch.

FIG. 1 illustrates an exemplary trial medical system 8 having an external trial SCS neurostimulation controller/generator device 10 equipped to deliver neurostimulation to a patient via a percutaneous lead 12 with a set of electrodes 14 implanted within the patient. In the drawing, phantom lines are used to illustrate implanted portions of lead 12; whereas solid lines illustrate external portions of the lead as well as other external components such as trial SCS device 10. In this example, lead 12 is routed through a protective implant site patch or bandage 16, which is mounted, affixed, adhered or otherwise sealed to the skin of the patient over the implant site of the lead, i.e. over the point where the lead penetrates the skin. That is, the term "implant site" herein refers to the puncture site or entry or exit point of a trial lead. It should be understood that the electrodes of the lead may positioned near internal tissues that are remote from the implant site and hence the implant site is not necessarily the same as the stimulation site. In the example of FIG. 1, a proximal end of lead 12 is connected to a disposable header component 18 of SCS controller 10. The lead passes into protective patch 16 through a top portion thereof and emerges from a bottom portion of the patch, with the electrodes of its distal end positioned adjacent nerve tissues to be stimulated. In this manner, the trial SCS device is externalized from the patient whereas the electrodes of the lead are internalized within the tissues of the patient, with the point of entry of the lead into the patient hygienically sealed under the protective patch. Other features and advantages of the protective patch are discussed below with reference to various examples.

Typically, the electrodes of a trial SCS lead such as percutaneous lead 12 are positioned near suitable nerves of the spinal column to allow for efficacious pain reduction via neurostimulation. However, in other examples, the electrodes might be placed elsewhere within the patient. Moreover, it should be understood that the percutaneous lead of FIG. 1 is merely exemplary. Four electrodes are shown in the example, although more or fewer electrodes can be employed. For example, the device might employ an eight-electrode Octrode™ lead, which is a type of linear eight electrode percutaneous lead provided by St. Jude Medical. Still further, in other examples, paddle electrode leads or other lead shapes or configurations might be used. Typically, the lead is removed upon completion of the trial period and replaced with a new lead if implantation of a permanent (i.e. chronic or long-term) SCS system is warranted. However, in some examples, the stimulation lead can be retained with the body, with the external device disconnected from the lead and replaced with a fully implantable neurostimulation controller that is then coupled to the implanted lead. See, for example, techniques described in U.S. patent application Ser. No. 13/940,727 of Nabutovsky et al., filed Jul. 12, 2013, entitled "Fully Implantable Trial Neurostimulation System Configured for Minimally-Intrusive Implant/Explant."

In the example of FIG. 1, trial SCS device 10 is equipped to communicate with an external controller/diagnostic instrument/programmer 20 using radio-frequency (RF) or other wireless signals to transmit data any collected by the trial device such as diagnostic data pertaining to its operation and/or to receive commands from the external instrument to activate, deactivate or adjust neurostimulation. The commands may specify various stimulation sets (Stim Sets) initially specified by a clinician. The Stim Sets specify SCS parameters for controlling delivery of SCS to nerve tissues of the patient to address the needs of the patient, such as to reduce pain or to achieve desired cardioprotective effects. The clinician or the patient can then change the Stim Sets using external instrument 20 via a wireless communication link 21 such as to change the amplitude, frequency or duration of stimulation pulses generated by the SCS device. The communication link may employ Bluetooth or other suitable wireless communication protocols. In some examples, the external instrument is a suitably-equipped tablet computer or smartphone, which may be referred to as a "Neuro External" device. See, for example, U.S. patent application Ser. No. 14/012,634 of Wu et al., filed Aug. 28, 2013, entitled "Systems and Methods for Low Energy Wake-Up and Pairing for use with Implantable Medical Devices." External instrument 20 may also be equipped to communicate with a centralized/remote data processing system 22 via the Internet or other suitable communication channels/networks to relay information to the primary care physician of the patient or to other appropriate clinicians. The centralized system may include or employ such systems as the HouseCall™ remote monitoring system or the Merlin@home/Merlin.Net systems of St. Jude Medical.

Although the example of FIG. 1 shows a trial SCS device 10 for stimulating the spinal cord, additional or alternative stimulation devices might be employed, such as devices for stimulating other tissues or organs within the patient. Some patients might additionally have an implantable cardiac rhythm management device (CRMD) such as a pacemaker, implantable cardioverter-defibrillator (ICD) or a cardiac resynchronization therapy device (CRT), which are not shown in the figure. Note also that FIG. 1 is a stylized illustration that does not necessarily set forth the precise locations of the various device components nor their relative sizes or shapes.

Figure 2:
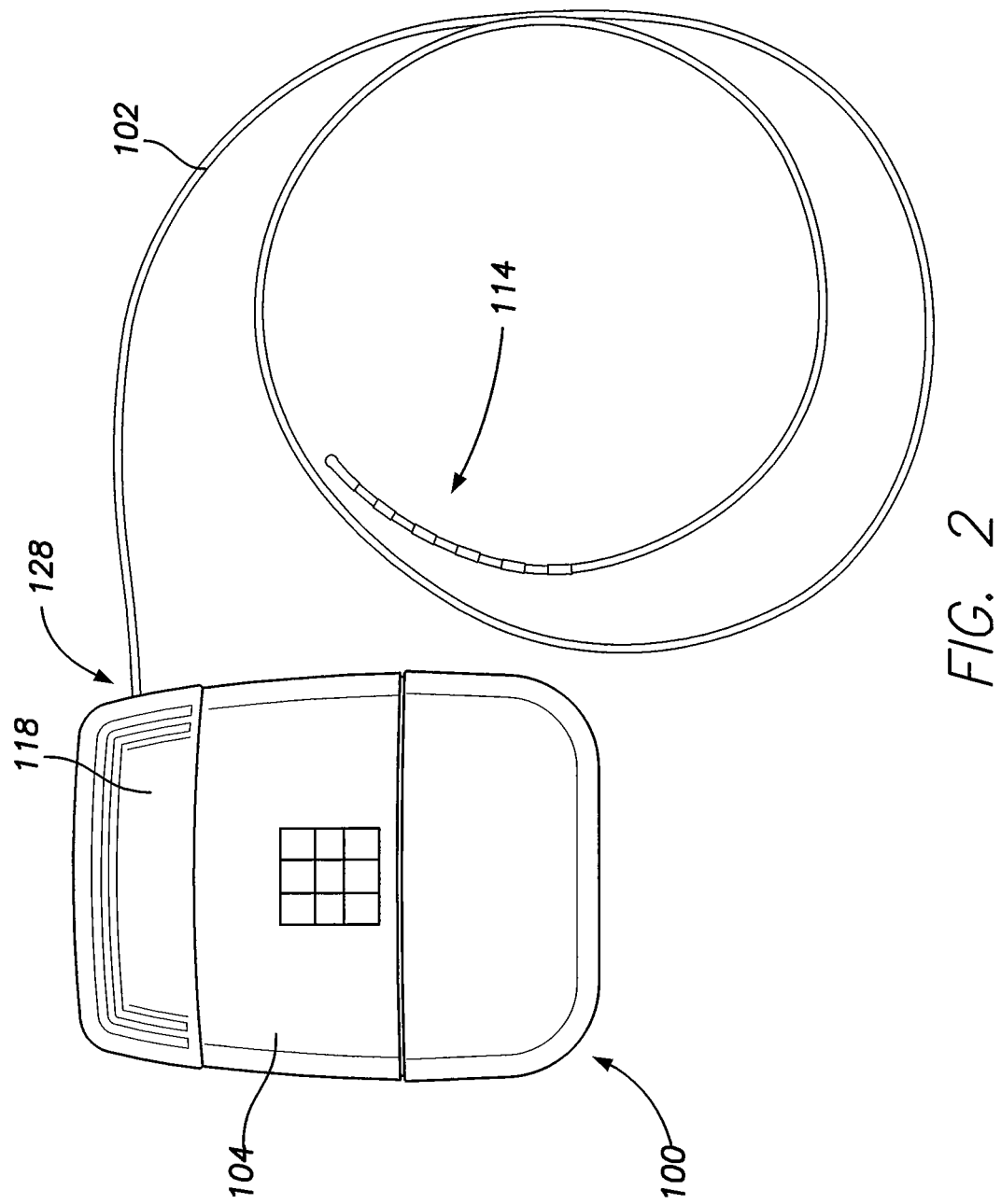
FIG. 2 illustrates an exemplary trial SCS device for use with the system of FIG. 1, shown with the neurostimulation lead attached to the device via a detachable and discardable header component.
Figure 3:
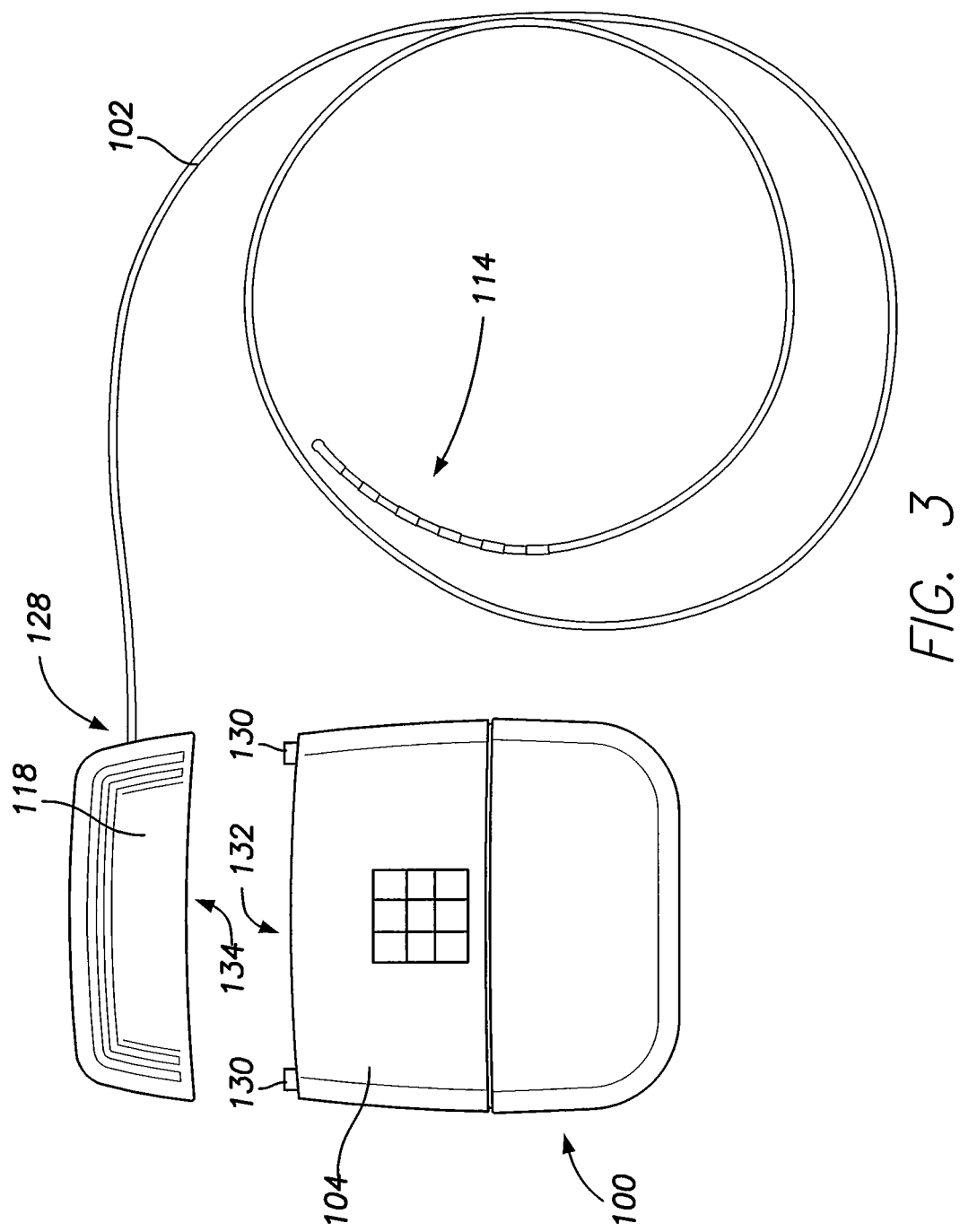
FIG. 3 illustrates the exemplary trial SCS device of FIG. 2, shown with the header component detached from a controller component of the device.

FIGS. 2 and 3 illustrate an exemplary trial SCS device 100 with a percutaneous lead 102 connected to a controller component (or body or unit) 104 of the SCS device via a detachable header component or unit 118. In the illustration of FIG. 2, header 118 is shown mounted or otherwise attached to controller 104. In the illustration of FIG. 3, the header is shown de-attached from the controller, exposing a pair of mounting tabs 130 employed to securely mount the header to the controller. Electrical terminals (not specifically shown) are provided along opposing mating surfaces 132 and 134 of the controller and the header, respectively, for relaying electrical signals between the controller and the lead via the header, including stimulation pulses. That is, the header includes internal electrical couplers or connectors (not shown in this figure) for coupling output terminals of controller 104 to corresponding terminals of lead 102 (also not shown in this figure). In this particular example, a proximal end 128 of the lead is permanently mounted into the header. Following completion of an SCS trial, lead 102 and header 118 are preferably discarded (since the lead may be contaminated with bodily fluids), whereas the controller 104 of the trial SCS device may be reused with another header/lead. In this example, the lead has a set 114 of eight electrodes, though more or fewer could be provided. The SCS controller of FIGS. 2 and 3 has various advantages. It is smaller than conventional belt-worn generators and can be taped to the patient's skin. The generator may be kept "out of sight" under the patient's clothing. The lead plugs directly into a disposable header and thus eliminates the need for an extension.

Figure 4:
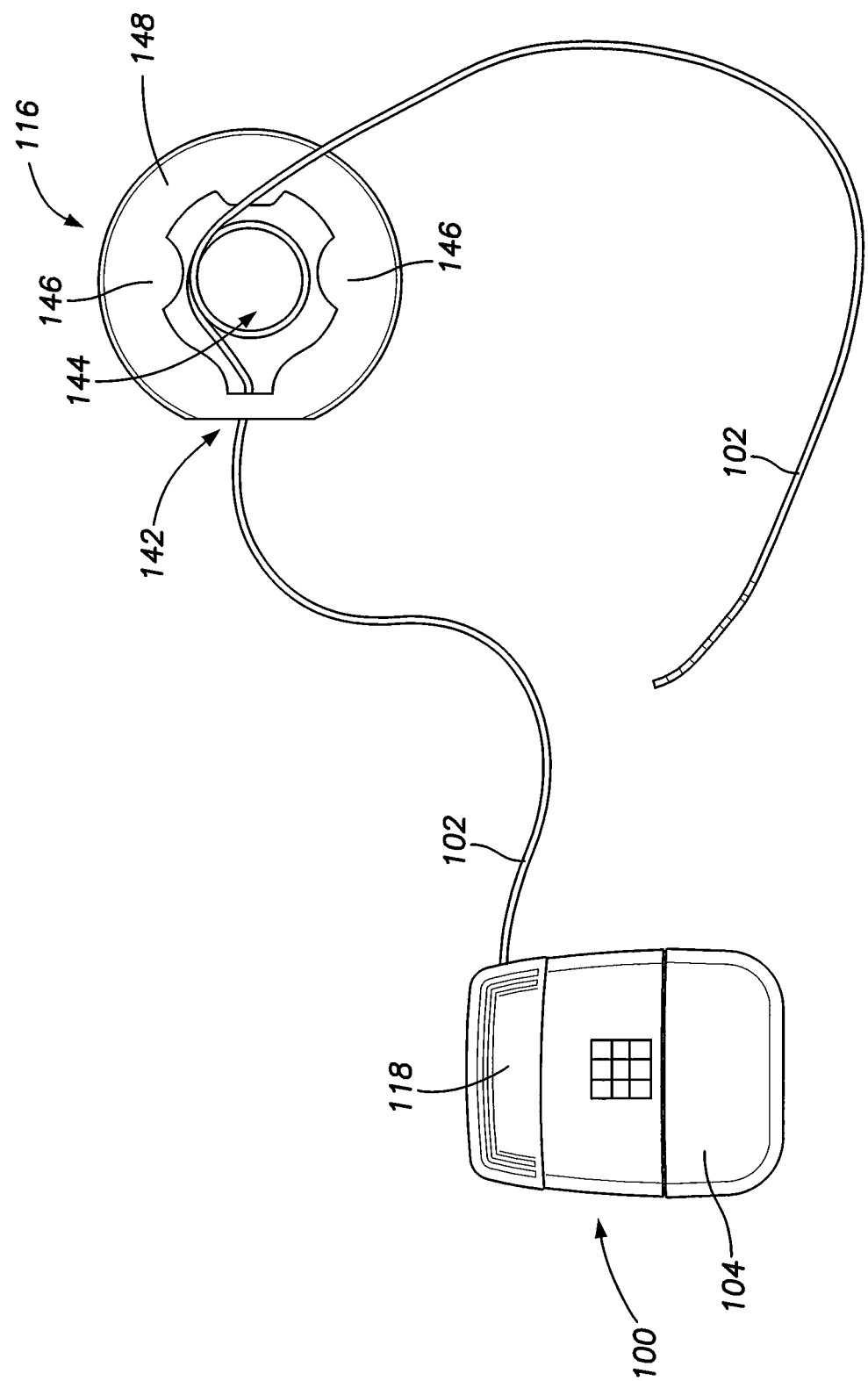
FIG. 4 illustrates the exemplary trial SCS device of FIG. 2 along with an example of the protective patch of FIG. 1, shown with the neurostimulation lead routed through the patch.

FIG. 4 illustrates exemplary trial SCS device 100 with lead 102 fed through a protective patch 116, of which the bottom or "skin side" portion of the patch is shown. As shown, lead 102 is fed from header 118 of SCS device 100 into the patch through an opening 142 in a top portion of the patch and then fed out of the patch through a central chamber 144. As already explained, in use, the distal end of the lead is implanted into a patient with the protective patch sealed over the point of entry into the skin of the patient. Bottom surface 148 may be provided with a medical skin adhesive for affixing the patch to the skin of the patient. Chamber 144 is generally circular and is sized and configured to hold a substantial length of the lead in a coiled arrangement (although, in this particular example, the lead is not shown in the coiled arrangement.) Coil retention tabs 146 are provided along bottom surface 148 to hold the coiled portion of the lead. The central chamber may also hold a medical gauze (not shown.)

Figure 5:
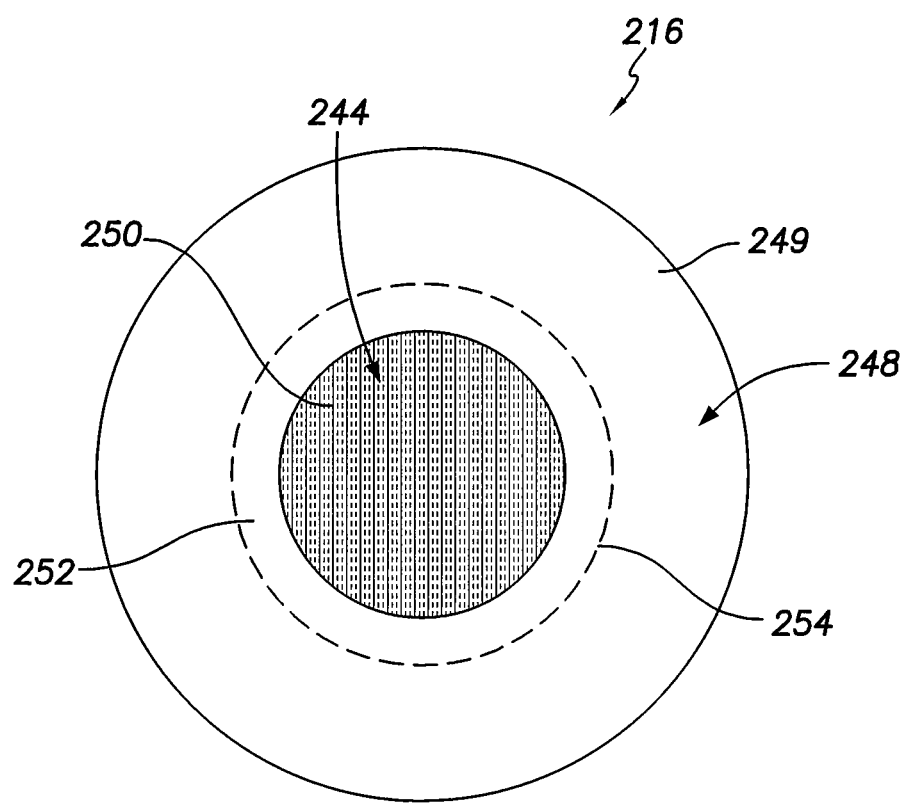
FIG. 5 is a stylized illustration of a bottom portion of the exemplary protective patch of FIG. 4 with medical gauze held with a chamber of the patch.

FIG. 5 provides a stylized illustration of the bottom portion of a protective patch 216 (without a lead shown.) Central chamber 244 includes a gauze 250 mounted therein. Bottom surface 248 of the patch includes a shaded portion representing a medical skin adhesive 249. A dotted line 254 shows the inner perimeter of the extent of the adhesive. Inner ring 252 of the bottom portion 248 of the patch provides a lead wrap overhang for holding a coiled portion of excess lead (not shown.) The lead wrap overhang may be provided in addition to, or as an alternative to, the retention tabs of FIG. 4.

FIGS. 6 and 7 provide cross-sectional views of a protective patch 316 (without the lead shown), particularly illustrating various internal components of the exemplary patch.

A top portion 320 of the protective patch is generally concave, as shown, with an elevated central portion 321 and a sloping peripheral portion 323. The central portion is elevated, in part, to accommodate central chamber 344, which may enclose gauze with antibacterial or antimicrobial agents as well as coiled portions of the implantable lead (neither of which is shown in this particular figure.) A peripheral portion of a bottom surface 348 of the patch includes a medical skin adhesive 349 to seal the patch over and around a point of entry of the lead into the patient (not shown in the figure.) Top portion 321 includes a passage or channel 325 formed within a part of peripheral portion 323 through which the lead is passed. The channel may have a substantially circular cross-sectional shape to accommodate the lead. The channel is preferably sized and shaped to snugly or tightly fit or hold the lead to prevent any significant passage of water or other fluids from outside the patch into its interior chamber (thus allowing the patient to shower) and to also prevent any significant passage of blood of other fluids from the interior chamber to the outside of the patch (thus helping to hygienically seal the puncture site of the lead.) An inner ring 352 extends into chamber 344 to provide a lead wrap overhang for holding a coiled portion of excess lead (not shown.) An upper surface of the chamber may be provided with a material 356, which can include additional antibacterial or antimicrobial agents. Note that the thin profile provides flexibility and patient comfort.

Trial Neurostimulation System with Protective Patch with Electrical Connector

Figure 8:
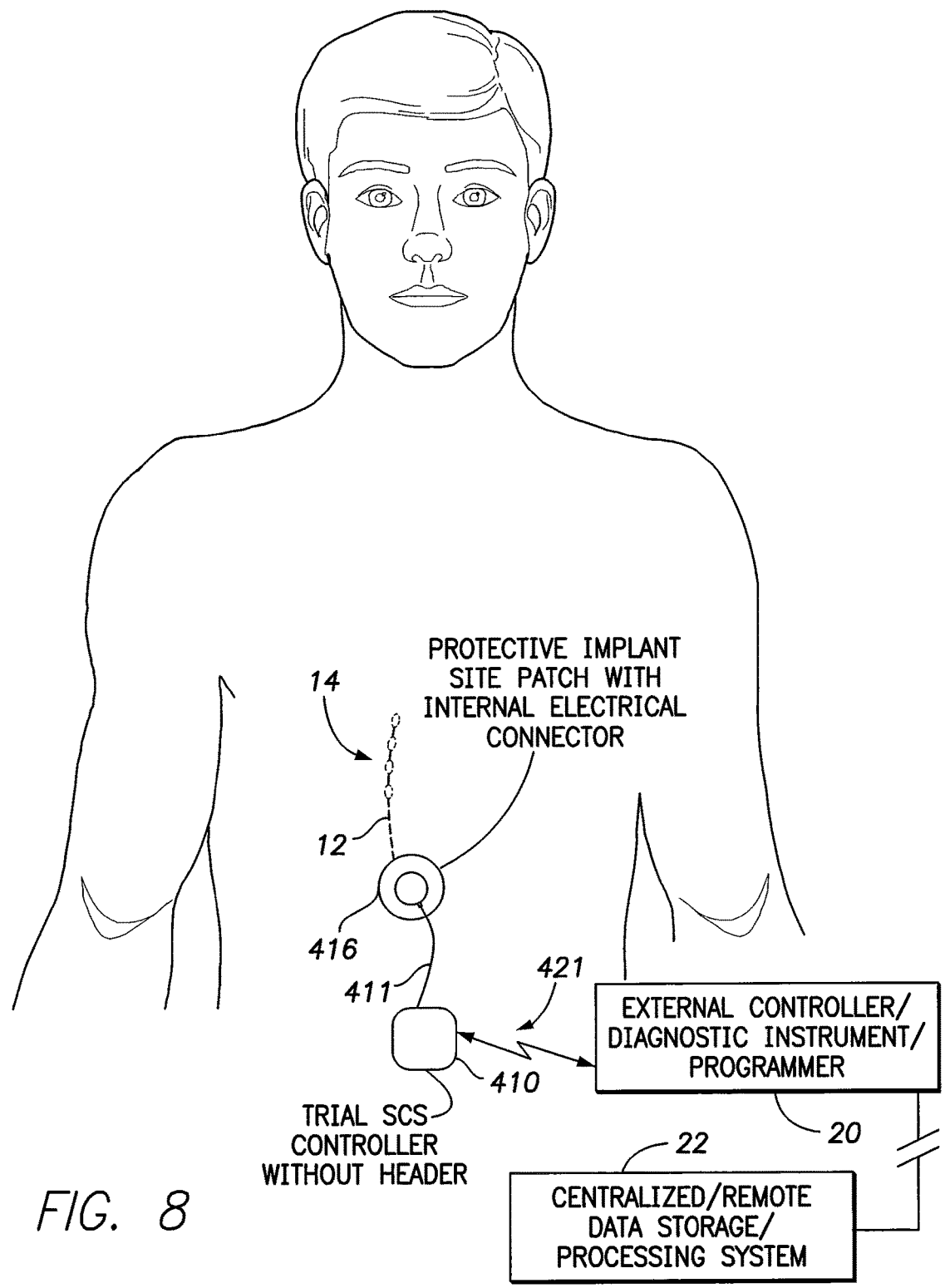
FIG. 8 illustrates another exemplary protective patch for use with a trial SCS device wherein an electrical connector is provided within the patch for electrically connecting a trial lead to a connection line of a trial SCS device.

FIG. 8 illustrates another exemplary trial medical system 408 having an external trial SCS neurostimulation controller/generator device 410 equipped to deliver neurostimulation to a patient via a connection line 411, which is electrically connected within a patch 416 to a percutaneous lead 12 having a set of electrodes 14 implanted within the patient. In this example, a proximal end of lead 12 is fed into a bottom portion of protective patch 416 but does not pass entirely through the patch as in the embodiment of FIG. 1. Rather, lead 12 is coupled into an internal electrical connector (not shown) within the patch, which also receives a distal end of connection line 411. A proximal end of line 411 is connected to SCS device 410. Since percutaneous lead 12 is not directly connected to SCS device 410, and hence there is no significant risk of contamination of the SCS device by the lead, a header of the type shown in FIG. 1 is not employed. However, in other examples, SCS device 410 could be provided with a header (with connection line 411 thereby coupled to SCS 410 via the header.) As with the example of FIG. 1, lead 12 is typically removed upon completion of the trial period and replaced with a new lead for further SCS. However, the lead could instead be retained with the body for connection to a fully implantable SCS device. Also, as in the example of FIG. 1, trial SCS device 410 can communicate with an external instrument 20 via a wireless link 21. External instrument 20 can communicate with a centralized system 22 via the Internet or other suitable communication channels/networks. Note also that FIG. 8 is a stylized illustration that does not necessarily set forth the precise locations of the various device components nor their relative sizes or shapes.

Figure 9:
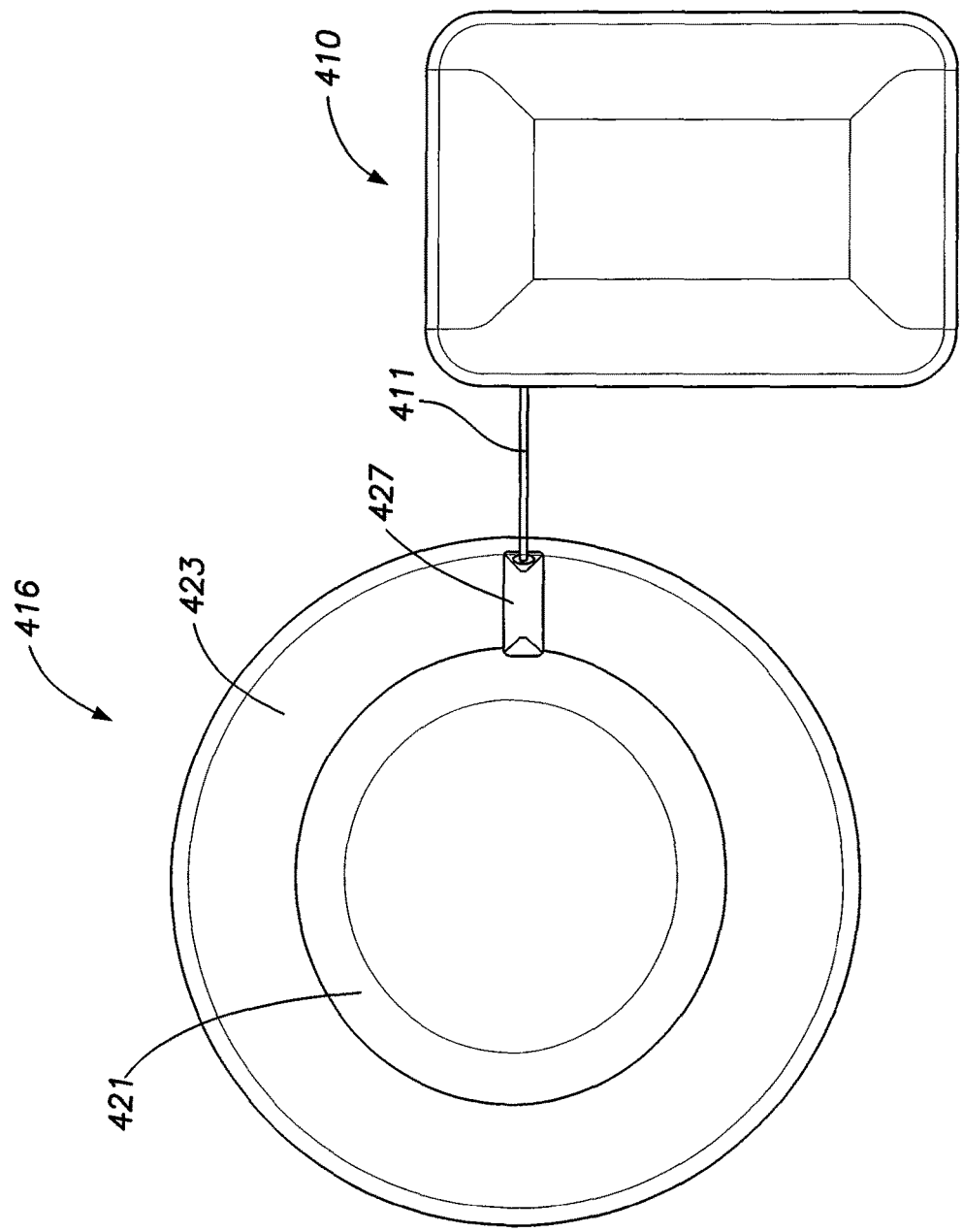
FIG. 9 is a stylized illustration of a top portion of an exemplary protective patch for use as the patch of FIG. 8, along with an SCS device equipped with a connection line for connecting to the protective patch.

FIG. 9 further illustrates exemplary trial SCS device 410 and protective path 416 of FIG. 8. Protective patch 416 includes a central elevated portion 421 surrounded by a sloping peripheral portion 423. A connection terminal 427 is provided to receive a distal end of connection line 411 from SCS device 410. The connection terminal is coupled internally to a proximal end of the percutaneous lead (not shown) either directly or via an intervening internal electrical connector (also not shown in this particular figure.)

Figure 10:
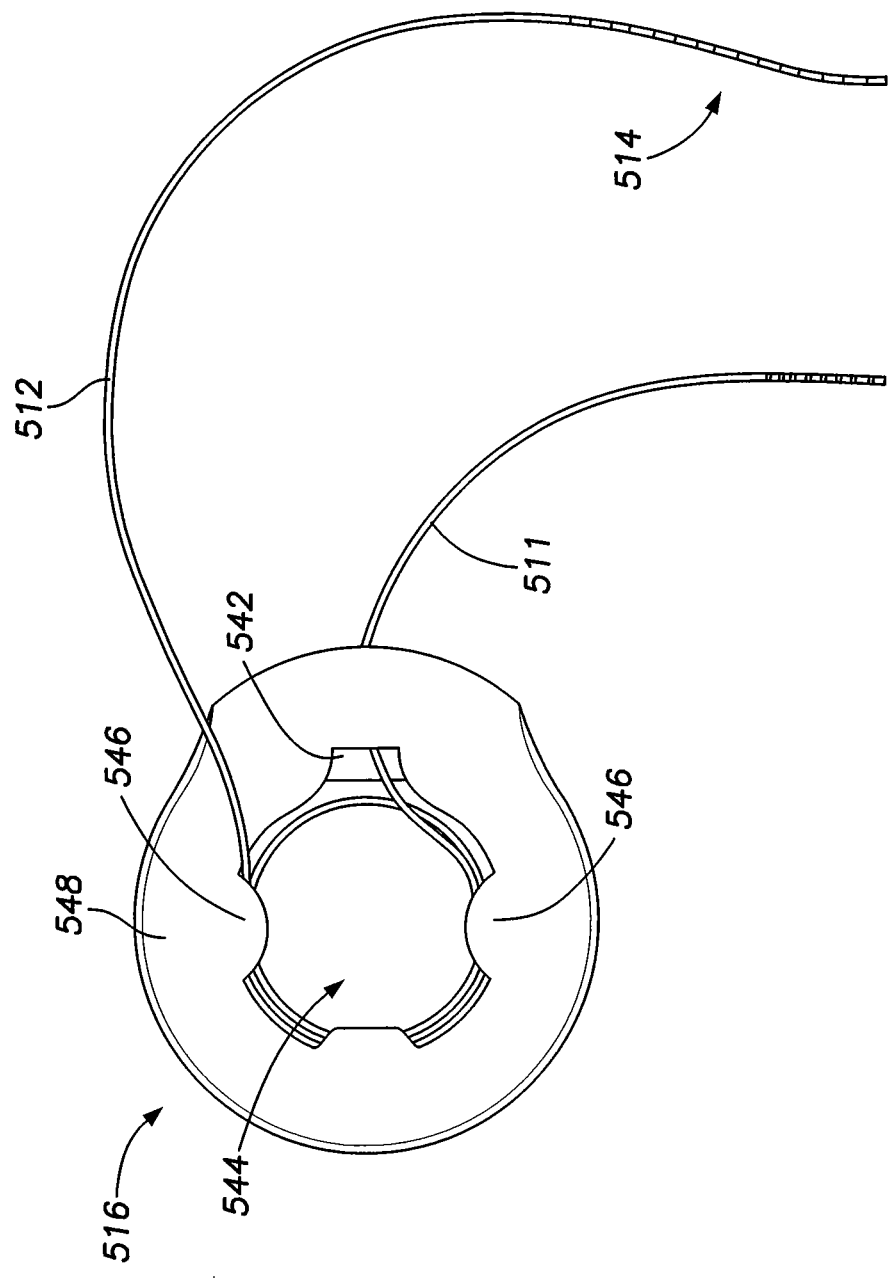
FIG. 10 illustrates an exemplary embodiment of the protective patch of FIG. 9, shown with a neurostimulation lead inserted into a bottom portion thereof and a connection line inserted in a top portion thereof.

FIG. 10 illustrates another example of a protective patch 516, of which the bottom or "skin side" portion of the patch is shown. As shown, a distal end of a connection line 511 is fed into a top portion of the patch through an opening 542 in a top portion of the patch. A proximal end of an implantable lead 512 is fed into a bottom portion of the patch through a central chamber 544. In this example, both implantable lead 512 and connection line 511 have portions coiled within the central chamber. Although not shown in this particular view, the distal end of connection line 511 and the proximal end of lead 512 are electrically connected via a suitable connector mounted within the protective patch. In use, the distal end of the lead having a set of electrodes 514 is implanted into a patient with the protective patch sealed over the point of entry into the skin of the patient. As with other examples described herein, a bottom surface 548 of the patch may be provided with a medical skin adhesive for affixing the patch to the skin of the patient. Chamber 544 is again generally circular and sized and configured to hold a substantial length of the lead in a coiled arrangement. Coil retention tabs 546 are provided along bottom surface 548 to hold the coiled portion of the lead (and any coiled portions of connection line 511 that may need to be held therein as well.) The central chamber may also hold a medical gauze (not shown.) Bottom surface 548 may be provided with a peel-away sheet or protective paper that is peeled off to expose the adhesive prior to affixing the patch to patient skin.

Figure 11:
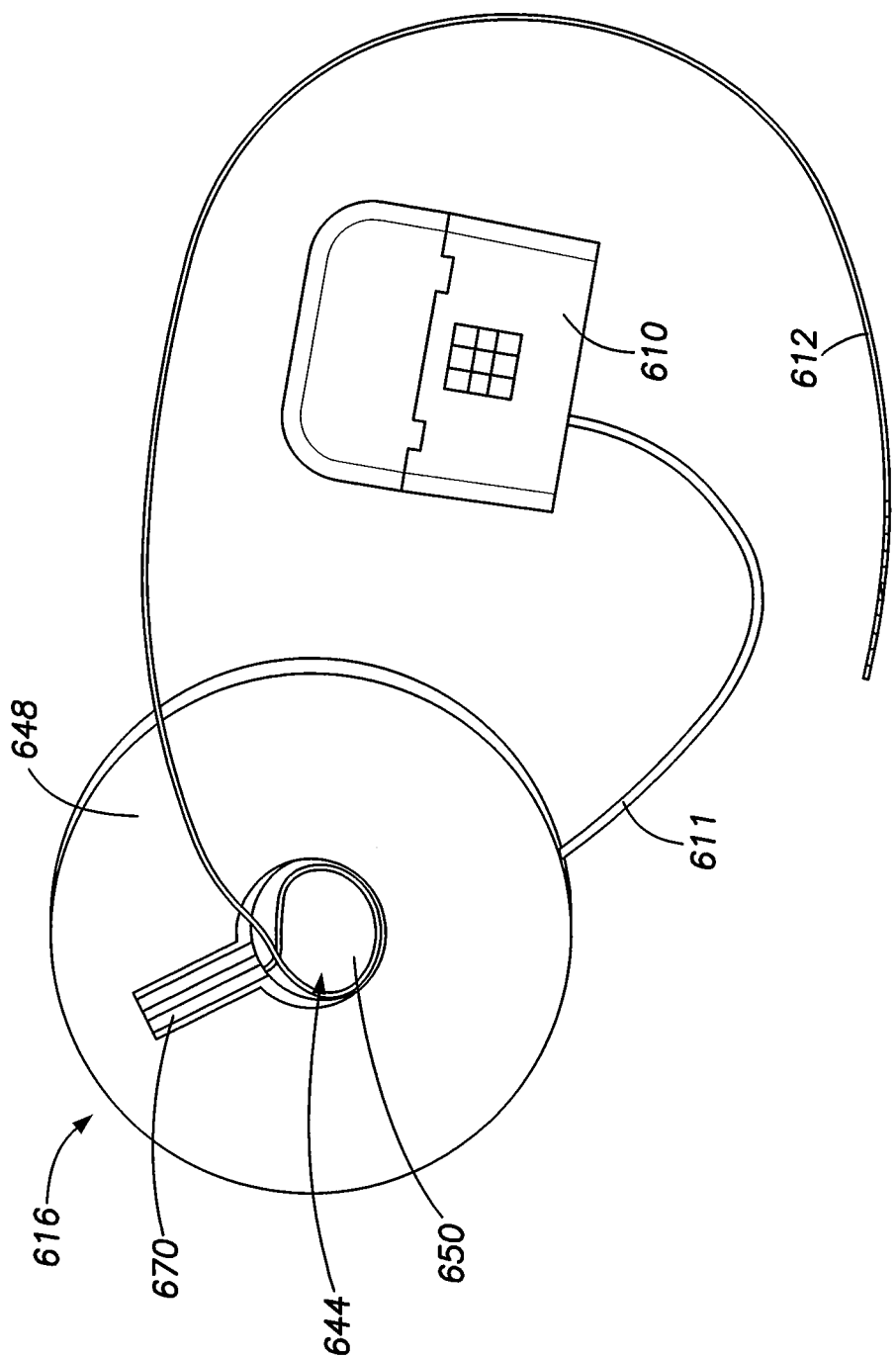
FIG. 11 illustrates aspects of an exemplary protective patch for use as the patch of FIG. 8 and particularly illustrating an internal electrical connector.

FIG. 11 provides yet another example of a protective patch 616, of which the bottom or "skin side" portion of the patch is again shown. A distal end of a connection line 611 from an SCS device 610 is fed into a top portion of the patch through an opening (not shown.) A proximal end of an implantable lead 612 is fed into a bottom portion of the patch through a central chamber 644, which also holds medical gauze 650. As shown, a distal end of connection line 611 and the proximal end of lead 612 are electrically connected via a suitable connector 670 mounted within the protective patch, adjacent to the central chamber. In the mockup shown in FIG. 11, a portion of the bottom surface of the patch is cut away to provide easy access to the connector for ease of attachment of the leads. In other examples, no such cutaway is provided so that the connector is isolated from patient skin. As with other examples describe herein, bottom surface 648 of the patch may be provided with a medical skin adhesive. Chamber 644 is again generally circular and sized and configured to hold a substantial length of the lead in a coiled arrangement. An inner perimeter of bottom surface 648 may extend partially over the central chamber to provide a lead wrap overhang.

Figure 12:
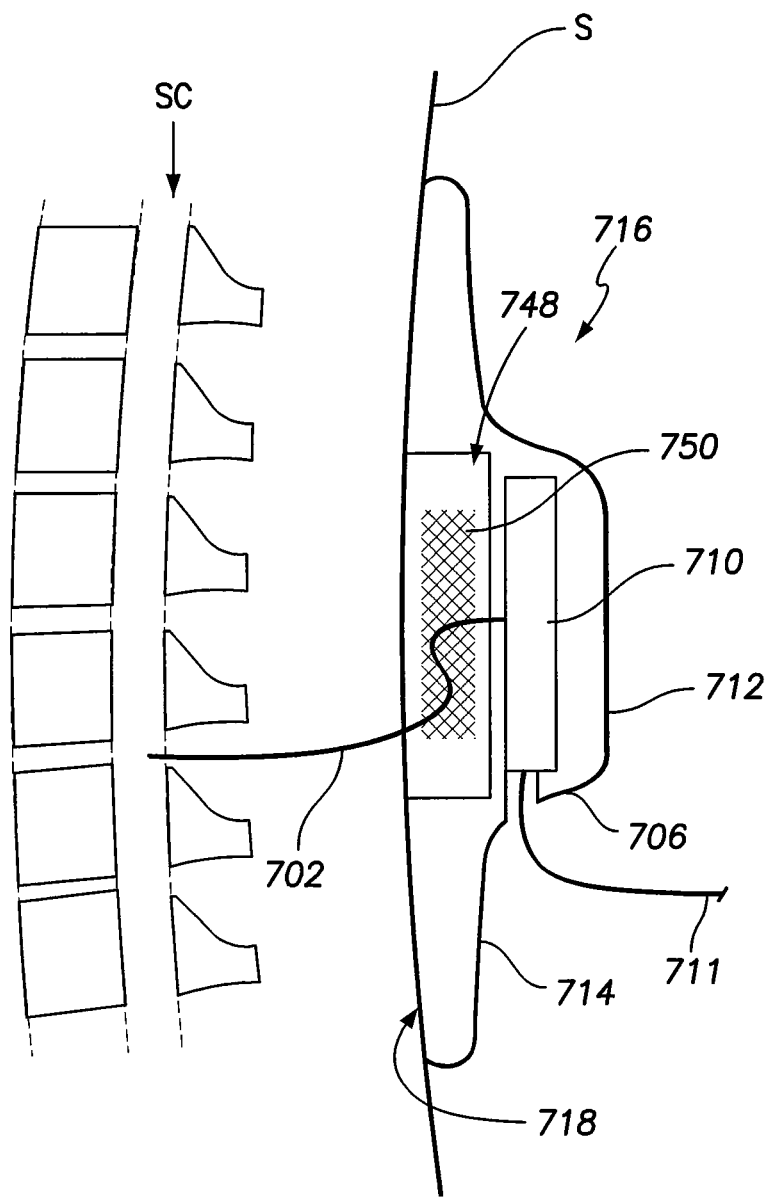
FIG. 12 illustrates another exemplary embodiment of the protective patch of FIG. 8, shown with neurostimulation lead and connection line.

FIG. 12 illustrates a simplified, example of an embodiment of a protective patch 716 provided with an internal electrical connector 710, shown schematically. In this example, protective patch 716 is attached to the skin S of a patient so that neurostimulation may be delivered to the spinal cord SC of the patient via a percutaneous lead 702. For the purposes of illustration, protective patch 716 and the spine of the patient are shown in cross-sectional view in FIG. 12. In this example, protective patch 716 includes a body member 706 and an electrical connector 710 located within the body member. A proximal end of lead 702 and a distal end of connection line 711 are both coupled into the electrical connector so that stimulation pulses and other signals may be routed therebetween. Body member 706 includes a central portion 712 and a peripheral portion 714.

In a typical implementation, central portion 712 holds the connection circuitry (e.g., connector 710) and serves to protect the puncture site where lead 702 passes through skin S, while a peripheral portion 714 is provided to affix the patch 716 to the skin S and provide a seal. However, the various components may be distributed in other ways and the various portions of the patch may serve different functions in other embodiments. The bottom, inner or "skin side" portion (i.e. the left side in FIG. 12) of body member 706 defines an opening or central chamber 748 (delineated by the dashed lines) for passage of lead 702. Chamber 748 also serves to protect the puncture site (e.g., the chamber provides a space to enable use of a gauze material over the puncture site as discussed above and also preferably provides space for coiling excess portions of the lead.) FIG. 12 shows only one chamber or opening 748 but multiple openings can be provided to accommodate passage of multiple leads into the patch for connection to electrical connector 710. This allows for covering additional sites along the spinal cord to increase coverage of possible pain relieving tracts along the spinal cord.

In some embodiments, body member 706 is constructed of a flexible (e.g., pliable) material. Through the use of such a material, patch 716 may readily conform to the contours of the patient's skin, even when the skin is subjected to movement during patient activity. Accordingly, patch 716 is preferably configured to be relatively comfortable for the patient to wear. Upon implant of lead 702, patch 716 is bonded to the patient's skin, upon application of pressure. Other fixation techniques may be used to attach a protective patch to a patient in Other embodiments. Examples of materials from which body member 706 may be constructed include one or more of: flexible molded polymer, silicone, polyurethane, soft poly vinyl chloride (PVC) or butyl rubber.

As noted, in some embodiments, patch 716 includes or is combined with absorbing material gauze (e.g., a bandage) for absorbing blood and other body fluids. The gauze material can have antibacterial or antimicrobial qualities. Alternatively, patch 716 could include circuitry to deliver an electric field that prevents formation of a biofilm and thus prevents infection. In some embodiments, the skin side of peripheral portion 714 includes a seal around the puncture site and/or around patch 716. Such a seal may protect the puncture site from infection and/or protect the components of patch 716. Preferably, the seal is waterproof to provide protection from water (e.g., to enable the patient to shower). In some embodiments, the electrical connector and any other electronics of the patch are waterproofed by encasing them in a water-repellent material. The patch can be disposable. In this manner, the patch could be changed every day or as needed. Although lead 702 and connection line 711 are typically releasably or detachably coupled to connector 710. In other embodiments either the lead or the connection line might be permanently coupled to the connector. As an example of a permanent connection, connector 710 may include a set of conductors (e.g., contacts or other types of conductors) to which a comparable set of conductors on lead 702 are electrically coupled while providing a substantially permanent (i.e., not readily removable) fixture. For example, the lead conductors may be soldered to contacts of connector 710. As an example of a releasable connection, connector 710 may include a releasable connector that includes contacts, whereby the releasable connector is configured to accept a complementary connector (e.g., a set of contacts) on lead 702. In such a case, lead 702 may be readily connected to or disconnected from the patch 700 to, for example, facilitate implanting lead 702 or changing patch 716.

Figure 13:
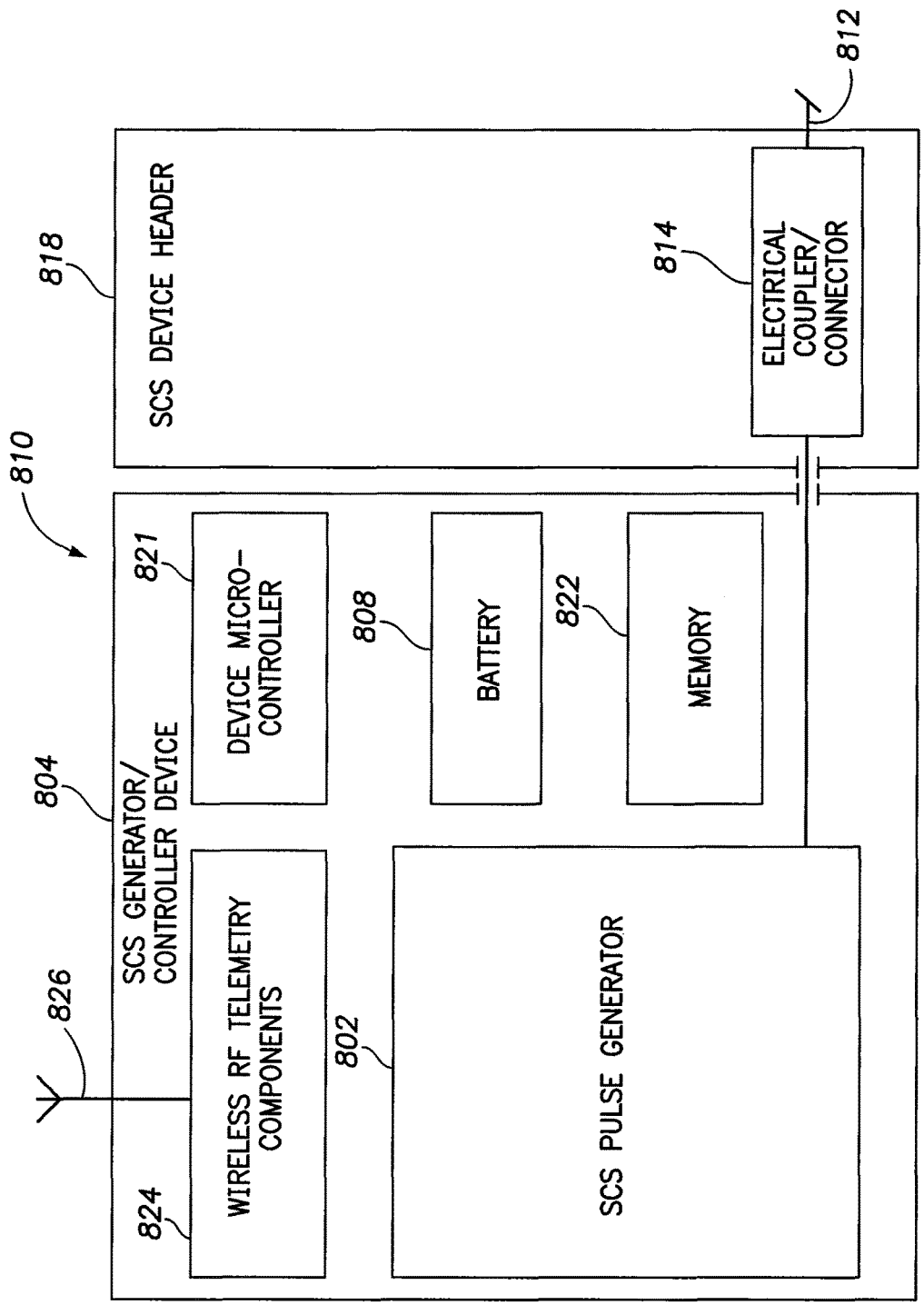
FIG. 13 is a block diagram illustrating pertinent components of the trial SCS device of FIG. 1.

FIG. 13 provides a block diagram illustrating exemplary and pertinent components of an SCS device provided with a header for use in delivering neurostimulation via a connection line or lead such as with the SCS device shown in FIGS. 1-4 above. Briefly, in this example, trial device 810 includes a pulse generator/controller 804 and a detachable and discardable header 818. An SCS pulse generator 802 of controller 804 is coupled to via an electrical connector 814 of header 818 to a stimulation lead 812. The pulse generator and other active components of the trial device receive power from one or more batteries 808 and operate under the control of a device microcontroller 821. With the exception of the connection between pulse generator 802 and connector 814, connection lines are not shown. Data (such as device diagnostic data and current stimulation parameters) are stored in device memory 822 and/or transmitted to an external instrument via wireless RF telemetry components 824 using an antenna 826 (which may be mounted on, or formed within, a portion of the housing of the device.) Typically, the wireless RF telemetry components are also equipped to receive signals from the external instrument via the antenna, such as SCS programming commands. As can be appreciated, various other components may be included within the SCS device to allow it to perform its intended functions, such as a device bus for relaying data and other signals among various components. The microcontroller, or some or all of the components, may be implemented using any suitable technology such as application specific integrated circuits (ASICs) or the like.

For further information regarding neurostimulation systems and techniques, see, e.g.: U.S. patent application Ser. No. 13/442,749 of Xi et al., filed Apr. 9, 2012, entitled "Systems and Methods for Controlling Spinal Cord Stimulation to Improve Stimulation Efficacy for Use By Implantable Medical Devices"; U.S. Patent Application Publication 2013/0325083 of Bharmi et al., entitled "Systems and Methods for Controlling Neurostimulation based on Regional Cardiac Performance for use by Implantable Medical Devices"; and U.S. Patent Application Publication 2010/0331921 to Bomzin et al., entitled "Neurostimulation Device and Methods for Controlling Same." See, also, techniques discussed in: U.S. Pat. No. 8,600,500 to Rosenberg et al., entitled "Method and System to Provide Neural Stimulation Therapy to Assist Anti-Tachycardia Pacing Therapy." See, also, U.S. patent application Ser. No. 14/226, 567 of Nabutovsky et al., filed Mar. 26, 2014, entitled "Systems and Methods for Assessment of Pain and other Parameters during Trial Neurostimulation."

FIGS. 14 and 15 summarize procedures for use with the various protective "guardian" patch embodiments of FIGS. 1-12. FIG. 14 provides an overview of techniques for use with a protective patch without an internal connector. Briefly, at step 900, a protective patch is provided with: a top portion having an opening for passage of an implantable trial SCS lead from a header of a trial SCS generator/controller into an inner chamber of the patch; a bottom portion configured to be detachably adhered to patient skin over an implant site and having an bottom opening for passage of the lead from the inner chamber into tissues of the patient at the implant site; and an adhesive formed on a peripheral portion of a bottom surface of the patch for sealing the patch over the implant site. At step 902, a distal end of the SCS lead is implanted into the patient at the implant site and the proximal end of the lead is fed through the protective patch for connection to the header of the SCS device around antimicrobial gauze. At step 904, the patch is adhered to the skin around the implant site using the adhesive to thereby protect and seal the site. At step 906, trial neurostimulation is delivered during a trial interval, then the patch, lead and header are removed and discarded and, if adequate pain mitigation was achieved during the trial period, a permanent (i.e. chronic or long-term) neurostimulation device/lead system is implanted.

FIG. 15 provides an overview of techniques for use with protective patch with an internal connector. At step 1000, a protective patch is provided with: a top portion equipped to receive an end of a connection line of a trial SCS device; a bottom portion configured to be detachably adhered to patient skin over an implant site and having an opening for receiving one end of an implantable trial SCS lead; an electrical connector equipped to connect the end of the connection line of the trial device with the end of the implantable trial SCS lead; and an adhesive formed on a peripheral portion of a bottom surface of the patch for sealing the patch over the implant site around antimicrobial gauze. At step 1002, a distal end of the SCS lead is implanted into the patient at the implant site and the proximal end of the lead is connected to a distal end of the connection line from the SCS device using the electrical connector of the protective patch. At step 1004, the patch is adhered to the skin around the implant site using the adhesive to thereby protect and seal the site. At step 1006, trial neurostimulation is delivered during a trial interval, then the patch and lead are removed and discarded and, if adequate pain mitigation was achieved during the trial period, a permanent (i.e. chronic or long-term) neurostimulation device/lead system is implanted.

The foregoing exemplary systems, methods and apparatus provide one of more of the following features or advantages: a) an SCS trial system that reduces infection by providing a Protective Bandage or Patch (i.e. a "Guardian") over the implant site; b) the system can allow for careful showering; c) the lead can be pushed through a sealed hole in the Protective Bandage and connected to a disposable header; d) alternatively, the Protective Bandage may include an SCS lead connector in the underside of the Protective Bandage and include an extension that connects to the Trial Lead Generator without a Disposable Header; e) the Protective Patch includes features that allow for a self-contained strain relief loop; f) gauze may be used to absorb body fluid in the lead compartment and allow for antibiotic or antimicrobial preparations to be included in the cavity over the wound; g) the Protective Patch helps prevent tugging on the lead that may lead to dislodgement and a failed trial; and h) the Protective Patch helps simplify the trial process and improve patient comfort during the trial.

The "Guardian" protective patch can be made of a pliable material such as silicone, such that it is comfortable to wear. The protective patch has an adhesive material that will adhere to the patient's skin without irritating it. One example of an appropriate material is a pressure sensitive adhesive (PSA). PSAs remain flexible after adhesion, which would maintain patient comfort. In addition, PSAs can be applied to the protective patch during manufacturing and bonded to patient skin later, upon application of pressure. The patch can be disposable or reusable. The patch can be combined with a bandage with absorbing material gauze (for blood and body fluids). The protective patch seals around the wound and protects during showering. The seal could be made of a material such as octylcyanoacrylate (Dermabond™) or N-butyl-2-cyanoacrylate (Indermil™) Alternatively, a simple tissue adhesive may be used such as is well known in the industry and used to adhere ICD skin paddles, electrocardiogram (ECG) electrodes, or medical adhesive tape. As noted, the protective patch can have antibacterial or antimicrobial qualities and can be impregnated with antibiotics, silver, or another anti-bacterial or antimicrobial substance.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A protective patch for use with an implantable trial neurostimulation lead for implant within a patient, the patch comprising:
    a top portion having an opening for passage of the implantable trial neurostimulation lead into an inner chamber of the patch; and
    a bottom portion configured to be detachably adhered to patient skin over a lead implant site and having an opening for passage of the implantable lead from the inner chamber of the patch and configured to be positioned into the tissues of the patient at the implant site;
    wherein the inner chamber is configured to hold a coiled portion of the implantable lead; and
    wherein the bottom portion of the patch includes a lead wrap overhang formed around the perimeter of the chamber to retain the coiled portion of the implantable lead.

2. The protective patch of claim 1, wherein the inner chamber is configured to hold a material for absorbing at least some body fluids emanating from the implant site.

3. The protective patch of claim 2, wherein the inner chamber includes a material having an antimicrobial agent.

4. The protective patch of claim 1, wherein the bottom portion of the patch includes retention wings formed around a perimeter of the chamber to retain the coiled portion of the implantable lead.

5. The protective patch of claim 1, wherein the bottom portion of the patch has a peripheral surface with a medical skin adhesive for sealing the patch over the implant site.

6. The protective patch of claim 1, wherein at least a portion of the protective patch is formed of flexible molded polymer.

7. The protective patch of claim 1, wherein the opening of the top portion of the protective patch is configured to provide a seal around the lead.

* * * * *